United States Patent [19]
Oita et al.

[11] 3,962,425
[45] June 8, 1976

[54] RUMINANT REPELLENT FROM ENZYMATICALLY PUTREFIED LIPOIDAL MATERIAL

[75] Inventors: Katashi Oita; James C. Lowe, both of Seattle, Wash.

[73] Assignee: Weyerhaeuser Company, Tacoma, Wash.

[22] Filed: July 17, 1974

[21] Appl. No.: 489,458

Related U.S. Application Data

[63] Continuation-in-part of Ser. No. 291,058, Sept. 21, 1972, abandoned.

[52] U.S. Cl. .................................... 424/94; 424/95; 424/104; 424/110
[51] Int. Cl.$^2$ ........................................ A61K 37/48
[58] Field of Search ................ 424/95, 94, 104, 110

[56] References Cited

UNITED STATES PATENTS

| | | | |
|---|---|---|---|
| 2,086,670 | 7/1937 | Grimes | 424/172 |
| 3,041,174 | 6/1962 | Ehlert | 99/7 |

OTHER PUBLICATIONS

Lesser—Animal repellents "Soap & Sanitary Chemicals" 9–1949, pp. 123–127 & 149–151.

*Primary Examiner*—Leonard Schenkman
*Attorney, Agent, or Firm*—Christensen, O'Connor, Garrison & Havelka

[57] ABSTRACT

A ruminant repellent composition effective to discourage browsing of edible material, especially living vegetable matter, is the decomposition product of a lipoidal material admixed with a lipolytic enzyme. One such composition is produced by admixing fish, such as whole salmon, with a source of lipolytic enzyme, such as visceral enzyme from feeding fish, or pancreatic enzyme derived from hog or beef pancreas. The effectiveness of the mixture can be increased by admixing additional lipoidal material such as fish oil, for example, tuna oil with the fish prior to decomposition. The active portion of the decomposition product of the lipoidal material and the lipolytic enzyme can be extracted with a water immiscible, organic solvent, such as dichloromethane, to separate the water soluble phytotoxins present in the decomposition product and to concentrate the active ruminant repellent components from the decomposition product.

19 Claims, No Drawings

RUMINANT REPELLENT FROM ENZYMATICALLY PUTREFIED LIPOIDAL MATERIAL

BACKGROUND OF THE INVENTION

This application is a continuation-in-part of the copending application, Ser. No. 291,058, filed Sept. 21, 1972 (now abandoned), assigned to a common assignee, and expressly incorporated herein by reference.

The present invention relates to a method of treating material normally eaten by free roaming ruminants, such as members of the deer family, to discourage such ruminants from browsing the edible material.

In those agricultural industries which grow crops, such as timber or food in regions adjacent to or within areas having a high ruminant population, the yearly loss of usable plant life to browsing or grazing by ruminants reaches staggering proportions. It has been estimated that the irreversible loss of timber resulting from ruminant browsing, either by stunting of growth or entirely killing the trees, exceeds many millions of dollars per year. This loss is caused primarily by members of the deer family, which browse on timber producing trees, such as Douglas Fir seedlings, during the late fall and winter seasons, and which selectively browse on the current growth of timber producing trees in the spring and early summer. The timber industry has been seeking a way to prevent browsing by ruminants, especially members of the deer family. A variety of compositions have been tried as ruminant repellents, which have met only with limited success.

The objects of this invention are broadly to provide a ruminant repellent which alone or in combination with other compositions will effectively discourage browsing by ruminants of edible materials such as trees, and to provide a ruminant repellent composition which is more effective than those of the prior art. Further objects of the present invention are to provide a ruminant repellent concentrate which has little or no phytotoxicity or mammalian toxicity; to provide a relatively low cost method for producing a ruminant repellent; to provide a ruminant repellent which is effective to discourage browsing of timber producing trees by ruminants; to provide a ruminant repellent composition which is easily applied to edible material; and to provide a ruminant repellent composition which can be relatively easily handled and processed.

SUMMARY OF THE INVENTION

The present invention therefore provides a method for discouraging ruminants from browsing edible material normally eaten by ruminants, which comprises contacting the edible material, or at least the region adjacent to the edible material with an amount of a repellent composition effective to discourage the ruminants from browsing the material, the active ingredient in the ruminant repellent comprising the putrescent product of a mixture of animal lipoidal material and a lipolytic enzyme. Preferably the enzyme is present in the mixture in an amount in excess of the lipolytic enzyme occurring naturally in the material. The active repellent component can be concentrated, and at the same time isolated from phytotoxins present in the putrescent product, by solvent extraction with a substantially water immiscible, organic solvent. The preferred lipoidal material comprises a mixture of whole fish and fish oil in excess of the fish oil present in the whole fish. The preferred lipolytic enzyme is that derived from the viscera of feeding fish.

DESCRIPTION OF PREFERRED EMBODIMENTS

Definition of terms: The following paragraphs will define certain of the terms utilized herein. The definitions are not exclusive but are intended to be used as a guide to one of ordinary skill in the art in understanding, making and using the invention. The term "lipid" includes neutral lipids, compound lipids such as phospholipids, and steroids such as cholestrol and its esters. The neutral lipids include fats and oils, which yield fatty acids and glycerol upon hydrolysis. Compound lipids such as the phospholipids yield fatty acids, glycerol, phosphoric acid and nitrogenous compounds upon hydrolysis. The term "lipoidal material" is used to define a mixture, chemical complex, or other composition which contains lipids in their naturally occurring form. "Animal lipoidal material" is that lipoidal material obtained from an animal source.

The terms "putrefy" and its derivatives are used to describe the chemical reaction (normally known as putrefaction) which occurs when lipoidal material undergoes an essentially uncontrolled microbiological decomposition. Among many known and unknown decomposition reactions which occur during putrefaction is the hydrolysis of lipids to their component compositions. A "lipolytic enzyme" is an enzyme which serves to catalyze the hydrolysis of lipids. For purposes of this specification the term "lipase" is interchangeable with the term lipolytic enzyme. The term "visceral enzyme" includes one or more enzymes which are present in the digestive tract of a living, feeding animal or an animal which is dead but had been actively feeding prior to its death. As used herein, for example, the visceral enzyme of feeding fish are those enzymes present in the digestive tract of a fish which is actively feeding or was actively feeding immediately prior to its death. The term "pancreatic enzyme" includes one or more enzymes which are present in the pancreas of animals such as hogs or cattle.

The term "repellent" or "repellent composition" as used herein is a composition of matter, including mixtures, which effectively repels or discourages animals from foraging or browsing upon edible materials. The terms "edible material" is herein primarily to mean plant matter which is normally eaten and digested by animals. The term "ruminant" includes those animals such as deer, elk and members of the bovine species which have a ruminal digestion. A "ruminant repellent" according to the present invention is a composition of matter or mixture which effectively discourages browsing by ruminants of edible material to or around which the repellent has been applied. The term "browsing" as used herein means the effective removal of all or part of a leaf, twig, branch or other part of living plant matter or the biting into of other edible material. For purposes of the examples herein, a leaf is considered browsed if it is merely nipped from a branch or from its location in one of the tests and is thereafter deposited on the ground but not wholly eaten by the animal.

The term "extract" as used herein means to intimately contact a material containing a solute with a solvent immiscible with a least a portion of such material. During extraction the solute goes into solution with the solvent. The solvent is then removed from the insoluble portion of the material by phase separation or other physical separation processes. The solute can then be removed from the solvent by distillation or other conventional solute removal techniques. The term "water immiscible, organic solvent" is a solvent composition which is substantially immiscible with water in all proportions and which will dissolve certain decomposition products of lipids. Examples of suitable water immiscible, organic solvents for use with the present invention are provided below.

A "U.S.P. unit" is a unit of potency for pancreatic enzyme and is that amount of an enzyme which, when assayed, converts not less than its own weight of olive oil U.S.P. into fatty acids in one hour. The method for determining the U.S.P. value of an enzyme is described in an article by Willstatter, R., WaldschmidtLeitz, E. and Memmen, F., *Z Physiol. Chem.*, 125, 93 (1923). Olive oil U.S.P., 14th revision, 1950 is defined as containing an amount of free fatty acid in 10 grams which will require not more than 5 cc. of 0.1 N sodium hydroxide to neutralize it, as having an iodine value not less than 79 and not more than 88, as having a saponification value of not less than 190 and not more than 195, and having a solidification temperature range of dry fatty acids contained therein of between 17° and 26° C. "Steapsin" is a lipase concentrate extracted from hog pancreas and has a lipase value 3.5 times the U.S.P. unit defined above. The temperature and pH optima for enzyme activity of Steapsin on an emulsified substrate are 45° to 50° C., and 5.0 to 7.0, respectively.

The term "carrier" is used to define a composition or mixture of materials which may be used to dilute a repellent composition to enhance the application characteristics of the repellent composition. Both water immiscible and water miscible solvents can be used as carriers. The term "formulate" is utilized herein to define the process by which the repellent composition is combined and/or suspended in a carrier. "Formulation" is used to define the resulting composition of matter. As will be seen later, the carrier may be primarily an aqueous mixture or solution or may be a nonaqueous mixture or solution. The term "contacting" is used in the context of applying the repellent composition or repellent and carrier to edible material, and is used to define the process by which the composition is deposited on the edible material or is caused to come into intimate contact with edible material.

A ruminant repellent is produced in accord with the present invention by the enzymatic putrefaction of an animal lipoidal material. To produce a ruminant repellent an animal lipoidal material is admixed with a lipolytic enzyme. If lipolytic enzyme occurs naturally in the original lipoidal material, the amount of lipolytic enzyme admixed is in addition to that which may naturally occur in the lipoidal material. The mixture is then allowed to putrefy. Preferably, the source of lipoidal material is finely divided or comminuted and is placed into admixture with a finely divided or communited source of lipolytic enzyme. Sources of lipolytic enzyme include those enzymes present in the viscera in feeding fish, and those enzymes derived from hog or cattle pancreas. If desired, a relatively pure, commercially available, lipase can be effectively utilized.

In accord with one embodiment of the invention, whole fish, including the head, tails and viscera, is comminuted and placed in a holding tank. A lipolytic enzyme from a source such as comminuted hog or beef pancreas is added to the comminuted whole fish. In this embodiment of the invention it is preferred that the ground or comminuted beef pancreas be added in an amount ranging from 1 to 10% by weight based on the amount of whole fish present. The hog or beef pancreas is comminuted to free the pancreatic enzymes therein. In addition, comminuted starting materials provide greater surface contact area, thus increasing the rate of enzymatic catalysis of the putrefaction reactions. The mixture of ground fish and pancreas is allowed to putrefy for a given length of time. If desired, the ground fish and pancreas can be combined with water, for example, in a 1:1 weight ratio of water to fish and enzyme to increase the liquidity of the original mixture and thus increase the rate of reaction.

Whole fish is preferred as a source of lipoidal material. The fish are preferably of the feeding type as opposed to those which are running or spawning since the latter have a relatively lower content of lipoidal material and have viscera with lower enzymatic activity. Successful results have been obtained with whole salmon, whole hake and whole dogfish. Other lipoidal material sources such as sheep flesh have also been successfully employed. The repellent activity of the putrescent product can be significantly increased if additional lipoidal material is added to the original mixture at the beginning of or during the decomposition period. Exemplary lipoidal materials are fish oils such as tuna oil, animal fats such as tallow and naturally occurring waxes such as wool grease. Such oils or waxes can be added in varying amounts and have been successfully used when incorporated in amounts up to 20% by weight based on the original mixture to be putrefied. Higher concentrations are undesirable since processing difficulties, such as pump clogging and the like, are encountered.

It has been found that an active repellent composition is produced from a mixture of fish and pancreatic enzymes in as little as from 1 to 7 days, although it is preferred that the material be allowed to putrefy for a time period of from 1 month up to 6 months, depending upon several parameters including the average temperature of the decomposing mixture. It is preferred that the mixture be allowed to completely putrefy, that is, change from its natural, partially solid state, having its original color, to a substantially liquid state, wherein the color of the decomposition product is gray to gray/-black.

The addition of lipolytic enzyme in excess of that naturally occurring in the lipoidal material provides distinct advantages. For example, the putrefaction time can be reduced to less than one half the time required for natural decay, i.e., from on the order of 1 year down to less than 6 months and normally down to less than 3 months. Also, a surprising increase in repellency, on the order of 400%, has been observed. Stirring of the mixture during putrefaction also greatly enhances the production of active repellent components. It is believed that this enhancement occurs since mixing maintains the mixture in a nearly homogeneous form or in a suspension, rather than in a phase separated condition, creating better equilibrium conditions for enzymatic hydrolysis of the lipids. In addition, the stirring tends to break up the solids to expose more lipoidal material to the action of the lipolytic enzymes.

Lipolytic enzyme can also be added to the system in the form of concentrated or extracted lipase in place of or in addition to pancreatic and visceral enzymes. An example of a lipase concentrate is Steapsin, defined above, which is available from Nutritional Biochemicals Corporation, Cleveland, Ohio. Lipase concentrates such as Steapsin can be added in amounts on the order or as little as 0.1% by weight based on the original lipoidal material present. Normally, lipase concentrates can be added in amounts in the range of 0.1 to 0.5% by weight, based on the lipoidal material present.

Preferred putrefaction conditions include an ambient temperature, and thus putrefaction mixture temperature, on the order of 70° to 100° F., although the present invention has been carried out at conditions where the ambient temperatures have fluctuated to below freezing. For example, a putrescent product containing active repellent compositions can be obtained in approximately 24 hours when the temperature of the putrefying mixture is on the order of 100° F. When the mixture temperature is reduced to around 60° F., an effective active repellent composition is not obtained until the mixture has been putrefying on the order of 12 days or more. Good results have been obtained in less than three months where atmospheric temperature conditions to which the mixture has been exposed have ranged from 40° to 90° F. When the putrefaction tanks are exposed to atmospheric conditions where solar heat is relied upon to maintain putrefaction temperatures, electrical or other auxiliary heaters can be utilized to maintain the temperatures between the optimum of 70° and 100° F. at all times.

After the original mixture has decomposed to a putrescent product, the product can be removed from the putrefaction tanks and moved to a processing area. It is preferred that the solid material such as skin, bones and other visceral tissue not acted upon by the lipolytic enzymes then be removed from the putrescent product. This is accomplished by screening or straining the putrescent product into liquid containers. For example, a first filtering through common chicken wire followed by filtering through common window screen is effective to separate the liquid and finely divided portion of the putrescent product from the skin, bones and other material.

The active repellent components of the filtered putrescent product are then preferably extracted from the filtered product with a water immiscible, organic solvent. It has been found that the active components in the filtered putrescent product are soluble in such a solvent, while undesirable decomposition products are retained in the remaining, unextracted fraction. Since water is preferably added to the putrefaction mixture and since water is present in starting materials such as whole fish, the fraction remaining after extraction is composed of water, water soluble materials, and a sludge which does not dissolve in either the solvent or water during extraction. The solvent fraction containing the active repellent components can be separated from the water fraction by conventional mechanical separation techniques such as centrifugation or decantation. The solvent and active components are then separated by evaporation of the solvent or by other suitable techniques. One means for removing the solvent from the active components is conventional flash distillation.

By extracting the fraction of the putrescent product which is soluble in the organic solvent, at least two advantages are obtained. First, a yield on the order of about 2.5% of usable product is obtained while over 97% of the liquid putrescent product can be discarded since the fraction soluble in the organic solvent retains most of the active repellent components. Second, a phytotoxic substance of unknown composition is produced during the decomposition of lipoidal material such as whole fish. Apparently this phytotoxin is water soluble and is only slightly soluble in the organic solvent. Thus, the additional advantage of phytotoxin separation is accomplished in the extraction process, leaving a fraction which is substantially nonphytotoxic, i.e., a fraction which causes relatively small damage to the needles of Douglas Fir trees upon application of the repellent composition in the concentrations disclosed herein.

Exemplary water-immiscible, organic solvents which can be used to extract the active components from the putrescent product are the halogenated hydrocarbons. The most preferred solvents are methylene chloride (dichloromethane), trichloroethane, chloroform and carbon tetrachloride. Other organic, water-immiscible solvents such as tetrahydrofuran, benzene, toluene can also be used for extracting the active components from the liquid putrescent product.

Both forms of the repellent composition, the putrescent product and the extracted fraction containing the active components, can be applied directly to edible material. It is preferred, however, that the repellent compositions be combined with a carrier and a binder. The binder serves as a "sticker", an agent which causes the active repellent composition to adhere to edible material. Both aqueous and nonaqueous carriers can be employed. It may also be necessary to employ an emulsifying agent to assure a thorough intermixture of the repellent composition when using an aqueous carrier. One effective repellent formulation which can be sprayed on edible material is formed by combining the repellent composition with a binder, an emulsifying agent, if necessary, and water in relative amounts ranging from 0.2 to 10% of the repellent composition, from 10 to 20% of the binder, and from 70 to 89.8% of water. A preferred aqueous formulation contains about 1.5% repellent composition, 13.5% binder and 85% water. The foregoing percentages and all other percentages given herein are by weight based on the total mixture unless otherwise designated.

A suitable binder which also serves as an emulsifying agent is "UCAR 180", an acrylic vinylacetate, nonionic emulsion copolymer containing a nonionic emulsifier. UCAR 180 is a tradename of and is available from the Union Carbide Company. Another binder, "Raeco No. 780 RB" having an asphaltic base is also effective. Raeco No. 780 RB is a tradename for an emulsified asphaltic base carrier containing at least about 56% by weight of asphalt solids in water. It is available from Raeco Products Company, 5700 Corson Ave. S., Seattle, Wash.

The binder can also be chosen from any of a large number of commercially available binders and emulsifiers, such as "Rhoplex AC 33", a tradename of the Rohm and Haas Company, Philadelphia, Pa. for its aqueous dispersions of acrylic co-polymers; "Acryloid F-10", a tradename of the Rohm and Haas Company for its acrylic ester polymers in a mineral spirits solvent. (Acryloid F-10 contains about 40% by weight of solid polymer); and "Carb-O-Set", an acrylic co-polymer containing a precise ratio of polar carboxyl groups and nonpolar groups, available from B.F. Goodrich Chemical Company, Cleveland, Ohio (Carb-O-Set 514H is an aqueous solution and Carb-O-Set 514A is a solution of the co-polymer in a solvent such as isopropanol). Suitable binders and emulsifiers should not be phytotoxic, should set up relatively rapidly to aid the active ingredient in readily adhering to the plant, and should be relatively versatile with respect to the ambient conditions under which it can be applied.

Although aqueous carriers are used with great effectiveness for the repellent composition of the present invention, an initial preformulation can be made by combining the repellent composition with a water miscible solvent to form a repellent concentrate. In addition, a binder can be added for the same purposes as in the aqueous formulation above, i.e., to provide better adherence of the repellent composition to the edible material after application. This repellent concentrate contains all the requisite active ingredients and contains all the ingredients necessary to provide a commercially usable and effective ruminant repellent. This concentrate can then be further diluted with the same water miscible solvent and applied directly to edible material. If desired, the repellent concentrate can also be effectively and economically diluted with water for application to edible material. In addition, the dissolved repellent composition and water miscible solvent can be mixed with various other repellents, such as a rabbit repellent. A typical rabbit repellent is tetramethylthiuram disulfide (hereinafter TMTD), commercially available from E.I. du Pont de Nemours and Company under the tradename "Arasan" and from Pennwalt Corporation, Philadelphia, Pa., under the tradename "Thiram". When the concentrate is combined with binders which are only partially miscible with water and when the concentrate is to be further diluted with water, it may be desirable, or necessary depending upon the nature of the binder system being utilized, to add a solubilizing agent such as ammonium hydroxide to form a more solubilized system.

Although preformulation with a water miscible solvent provides a more versatile repellent concentrate, any suitable solvent for the repellent composition can be employed to form the concentrate. If a water immiscible solvent is chosen, then dilution of the concentrate must be accomplished with the same solvent or a solvent which is miscible with the initially chosen water immiscible solvent. A suitable water immiscible solvent is "Chevron 250", a tradename of of the Chevron Chemical Company, San Francisco, Calif., for its organic solvent comprising about 94% by weight of paraffins and napthenes and about 6% by weight of toluene.

Water miscible solvents which can be utilized to form a repellent concentrate are abundant. One group of water miscible solvents are the alkyl alcohols having from one to four carbon atoms. Other solvents which can be utilized and which exhibit the same low toxicity characteristics are exemplified by diacetone alcohol, dichloroethyl ether, dioxane, cellosolve (a tradename of the Union Carbide Company for its ethylene glycol monothylether solvent), methyl ethyl ketone, and isopropyl acetate. Other effective but less preferred solvents, which may exhibit greater phytotoxicity or mammilian toxcity than the foregoing, are disclosed in an article by Gast, R., and Early, J., *Agricultural Chemicals*, 10, April, 42(1956), pp 42, 43, 136, 137 and 139, expressly incorporated herein by reference. All of the solvents listed in the foregoing article which are water miscible will form an effective solvent for the repellent composition of the present invention. However, as can be seen from the data provided in the referenced pages, several of the solvents have a relatively high phytotoxicity, and thus are not desirable from that standpoint. Characteristics of the solvent which are desirable for a commercial, sprayable repellent composition include ready biodegradability without leaving toxic residue, water solubility for most applications, and, a capability to solubilize the repellent composition. If a nonaqueous formulation is desired certain of the listed solvents which are not desirable from the water miscibility standpoint, such as ethylacetate and ethylene dichloride, can be employed.

The repellent formulations (both the aqeuous and nonaqueous formulations thereof described above) can be applied to two and three year old Douglas Fir seedlings, by conventional mechanical spraying apparatus. These formulations provide effective repellent properties when applied at the rate of 100 gallons of repellent formulation per 300,000 two year old seedlings and 100 gallons per 100,000 three year old seedlings. As another example, where seedlings are planted at a density of on the order of 600 to 700 trees per acre, 1 to 2 gallons per acre applied by hand-held sprayers can be utilized to effectively prevent browsing of new growth on such trees by ruminants. The same formulation has also been found effective when sprayed in concentrations of about 10 gallons per acre from a helicopter. The foregoing application levels of the repellent compositions and formulations are intended to be representative of effective levels of repellency. One of ordinary skill after reading the foregoing specification will be able to adjust these effective application levels depending on the type of crop, the weather conditions, terrain, ruminant population, and other variables known to him.

The repellent compositions (both the aqueous and nonaqueous formulations thereof described above) are also effective to discourage ruminants from browsing edible material even if not directly applied to the edible material. Ruminants are repelled from an area or region, to which they would otherwise normally be attracted because of the presence of edible material, if the ruminants encounter the presence of the repellent composition at the periphery of the area. When ruminants encounter the repellent at the periphery, they will refrain from crossing the periphery into the area or region containing edible material. This holds true whether the area is relatively large, as a tree nursery or plantation, or small, as an area of several square feet containing a single four year old tree.

The repellent composition, formulated as described above, can be applied to the periphery of the area in several ways. The foliage and/or the land along the peripheral portion of the area can be sprayed in a two or three foot wide or wider strip, which strip surrounds the area from which it is desired to repel ruminants. Alternatively, a "chemical fence" can be prepared to repel ruminants from a chosen area. To prepare such a fence the repellent composition is sprayed onto, spread onto, or absorbed in a piece of material, such as a length of fiber rope, which in and of itself has no repellent effect, i.e., is relatively inert. The rope or other material is then placed along the peripheral portion of the area from which it is desired to repel ruminants. As ruminants encounter the strip surrounding the area, or the rope placed around the area, they are repelled, preventing them from gaining access to the area, and thus, discouraging them from browsing any edible material which may be present in the area. Although any suitable type of material can be used as the substrate for the chemical fence, it is preferred that the material be of a nature which will retain effective amounts of the repellent composition. Thus, a natural fiber rope having good absorbent properties is desirable. The rope can be treated with the repellent composition by soaking it for a few hours in one of the foregoing repellent formulations. Thereafter, it can be strung along posts surrounding the area from which it is desired to repel ruminants.

In a like manner, the repellent formulations of the present invention can be used to divert ruminants from normal migration or range paths to guide them away from areas through which they might otherwise normally travel on a day-to-day or on a seasonal basis. For example, a strip several feet wide along a well traveled ruminant migration or range path can be sprayed with the repellent composition. The path of the sprayed strip can be located to cross over the normal migration path and lead into an area away from the region from which it is desired to repel the ruminants. As the ruminants travel their normal migration paths and encounter the strip sprayed with the repellent formulation, they will refrain from crossing the strip and will instead be diverted along the side of the sprayed strip in a direction away from the region from which it is desired to repel them.

BIOASSAY TEST PROCEDURES

The products produced in the following examples were bioassayed on deer according to the bioassay test procedures described below. For purposes of both bioassay test procedures, the percent of leaves browsed was determined by dividing the number of leaves in the original test sample into the number of leaves browsed and multiplying by 100%. In each series of tests the product tested was compared with a treated control. For purposes of the comparisons in Table I, the treated controls were the products of Examples I and II.

In both bioassay test procedures, the treated leaves were dipped in a formulation containing the repellent product produced in accord with the following examples. The binder was UCAR 180 unless otherwise noted. The formulations contained the ingredients in amounts indicated in Table I. The results of the bioassays are reported in Table I.

Although neither of the test procedures utilized coniferous trees as edible test samples, the results can be directly correlated to results on Douglas fir and similar trees. Among other reasons, the edible samples used in the test procedures were chosen because of ease of identifying browsed samples and deer diet preferences corresponding to seasonal changes. Adequate feed for the deer was maintained in the pens in addition to the test samples. This feed normally took the form of a pelletized feed supplement and loose alfalfa in self-feeding troughs.

TEST PROCEDURE "H"

A madrone or black oak branch containing several subbranches and having in total approximately 100 to 500 leaves was selected. A sub-branch containing at least 10 succulent leaves was chosen as the test sub-branch to be treated. The leaves were counted and tagged. A second sub-branch separated from the first treated sub-branch containing at least 10 leaves was also chosen as a control. Ten leaves were counted on this branch and were tagged so that they could be counted if later browsed or eaten. The 10 leaves to be treated were dipped or sprayed with the repellent formulation being tested. Great care was taken to prevent contamination of the untreated leaves, not only of the control but all the untreated leaves surrounding the treated sample.

The branches having treated leaves were placed in each of four adjacent pens, each containing the same number of deer. The number of deer in the pens as well as the maturity and sex varied among the several tests. The tests were duplicated in each pen and run at the same time. The results from the four pens were averaged to give the results in Table I. The tests were conducted until 100% of the untreated control was browsed.

TEST PROCEDURE "MC"

Twelve pairs of salal branches, each branch having exactly ten leaves, were placed in a predetermined location in a circle in each of two deer pens. The circles had a 9½ foot radius. Each of the pairs of branches was spaced 20 inches apart and placed in a container so that the branches could be retained. The spacing between adjacent pairs was 40 inches. One of the 12 pairs was untreated, leaving it as a control. One branch of each of the other 11 pairs was treated with a repellent material being tested. The remaining branch of each pair was left untreated as an adjacent control. Generally more than one circle was set up at a time in each of two deer pens adjacent each other. A circle in the first pen was duplicated by a circle in the second pen. The test procedure was continued until approximately 80% of the untreated control sample was browsed.

EXAMPLE I

Whole spent salmon were placed in a large polyethylene bag which was fitted inside a 55 gallon steel drum. The whole spent salmon were obtained from fish hatcheries in the Pacific Northwest after the eggs and sperm were stripped. Initially the drums were filled with the whole fish, but later the decomposed fish settled in the drums to produce approximately 30 gallons of material per drum. Approximately 50 drums were filled with the whole spent salmon. The drums were located outside and were exposed to prevailing atmospheric conditions. The drums were filled in March when ambient temperatures ranged from 30° to 60° F. Prior to placing lids on the steel drums, the polyethylene bags were tied loosely so that gas produced in decomposition could escape. The drums were loosely capped with a steel lid from mid-March through late August. The temperature during this period ranged from 30° to 90° F. During at least two of these months the average daily temperatures were in the range of from 60° to 90° F.

During late August, the covers were removed from each of the steel drums. At this point in time the salmon were nearly putrefied. There were traces of pink salmon meat present and the general physical shape of the salmon remained. The polyethylene bags were opened and the contents of the bags were thoroughly stirred with a masonry stirrer powered by a half-inch electric drill. Substantially all of the remaining solid matter was broken into pieces.

Thereafter the large particles were screened from the contents of each of the barrels by pouring the contents of the bag across a hexagonal chicken wire screen (1 inch openings) into a trough. The large bones and the large pieces of undecomposed salmon, primarily the skins and the bones, were removed on the chicken wire. The liquid and other particulate matter in the trough was then pumped into a large steel bin. Approximately 1500 gallons of putrefied fish were placed into the bin. The contents of the bin were then mixed in approximately a 1:1 ratio (by weight) with methylene chloride. The contents of the bin were thoroughly mixed by placing the intake of a 600 gpm trash pump at the bottom of the bin and placing the outlet near the top of the bin. The pump was run for several hours. The contents of the mixture in the bin were then filtered through a screen having approximately ⅛ inch openings. The filtered material was then pumped into 500 gallon drums. The putrefied fish/methylene chloride mixture from the drums was then thoroughly mixed in a 1:1 weight ratio with water (one part water to one part fish/methylene chloride mixture), producing a two-phase system.

Thereafter the mixture of water, methylene chloride and putrefied fish mixture was centrifuged to separate the water phase from the methylene chloride phase. The centrifuge used was a continuous DeLaval Type BRPX 207-19S-60. The centrifuge was operated at approximately 2000 rpm. Approximately 3000 pounds of material per hour was run through the centrifuge. The bowl was opened periodically to remove built-up sludge, primarily grit, bone, skin scales from the putrefied fish. The light phase separated by the centrifuge was the water phase and was discarded. The heavy phase, comprising the methylene chloride and its solute was taken from the centrifuge and was stored in two 300 gallon tanks.

The methylene chloride phase was then run through a commercial, batch type, flash evaporator. Approximately 200 to 400 gallons of the methylene chloride phase were placed in the evaporator per batch. The evaporator was run until the temperature of the bottoms product (the active product) increased to 190° F., after which the evaporator was run for approximately 2 to 5 minutes more. The active product was then placed in storage drums while still hot. The active product appeared to have a heavy grease consistency when cooled down in the storage drums. Approximately 300 pounds of active decomposition product was obtained. This represents approximately a 2 to 2½% yield from the original fish.

EXAMPLE II

In mid-February approximately 13,000 pounds of ground whole frozen salmon were placed in each of eight 3,500 gallon tanks exposed to the atmosphere and to sunlight. The frozen ground fish may not have completely thawed until approximately two months later in mid-April. About 260 pounds of shredded beef pancreas (about 2% by weight based on the salmon) were added to each of the tanks during mid-April. In mid-May a large tarp was placed over each of the 3,500 gallon tanks. A kerosene fired 80,000 BTU forced air space heater was inserted under the tarp to heat the area surrounding the tanks. This was repeated for about three days during the month of May. The tanks were heated to initiate the enzymatic decomposition of the material in the tanks. In mid-June the tanks, which had been previously painted yellow, were painted black to increase absorption of solar heat.

Early in August the partially decomposed product was taken from each of the 3,500 gallon tanks and was screened through a ⅛ inch mesh screen into a trough. The material was then pumped back into clean 3,500 gallon tanks. About 5% by weight, based on the contents of the tanks, of tuna oil was then added to each tank. Beginning during the second week in August the material was stirred about once a week with a masonry stirrer.

During the first week in September the fish/tuna oil mixture had putrefied to the extent that no pink salmon meat could be seen. The mixture appeared grayish-black in color. The putrescent product was then extracted with methylene chloride. The methylene chloride was added to the putrescent material in approximately a 1:1 ratio (by weight). Water was added up to a 1:1 weight ratio (water to putrescent product plus methylene chloride) to improve the pumping and processing consistency of the product. The methylene chloride, putrescent product and water were then thoroughly mixed. The methylene chloride heavy phase was then removed in a centrifuge as in Example I. The methylene chloride heavy fraction was then flash evaporated as in Example I, yielding an active decomposition product weighing approximately 3,720 pounds.

EXAMPLE III 1,112 grams of fresh ground salmon and 22.5 grams (2% by weight based on the salmon) of ground beef pancreas were admixed. Thereafter 56 grams of tuna oil (5% by weight based on salmon) were admixed with the mixture of salmon and pancreas. These materials were allowed to stand together and decompose for a period of 21 days. An active product was then extracted from the foregoing mixture with approximately 1,200 grams of methylene chloride. The methylene chloride was then evaporated from the active fraction utilizing a laboratory rotary evaporator. Approximately 55 grams (6.3% yield) of the active decomposition product was obtained. The active decomposition product is that portion of the total putrescent product which was methylene chloride soluble.

EXAMPLE IV 10,240 grams of fresh ground whole salmon were admixed with 55 grams of a lipase concentrate. The mixture was allowed to decompose for a period of 20 days at ambient room temperatures of 60° to 70° F. to produce an active product having effective repellency. The lipase concentrate used was Steapsin, defined above. The product was not extracted.

EXAMPLE V 30 gallons, approximately 240 pounds, of fresh ground salmon were mixed with 2% (by weight based on the salmon) of fresh ground beef pancreas. The material was allowed to putrefy for 12 days. A yield of 1.5% by weight (12 grams) of repellent product was obtained upon extraction of 308 grams of the putrefied mixture with 296 grams of methylene chloride and evaporation of the methylene chloride from the active fraction.

EXAMPLE VI 2,871 grams of the fish/pancreas mixture prepared in a manner identical with Example V were additionally admixed with 319 grams of tallow. After putrefying for 10 days, 254 grams of the putrefaction product were extracted with 250 grams of methylene chloride. A yield of 27 grams of methylene chloride soluble active decomposition product was obtained after the methylene chloride was evaporated.

EXAMPLE VII

A mixture of 210 grams water, 45 grams tuna oil, 45 grams of gelatin hydrolysate, enzymatic, No. 3731 (ordered from Nutritional Biochemicals Research biochemicals catalog) and 0.5 gram of lipase (Steapsin, a tradename defined above). This mixture was allowed to decompose for 10 days. The active putrescent product was not extracted.

EXAMPLE VIII

The procedure of Example VII was repeated, omitting the lipase.

As can be seen from the bioassay results set forth in Table I, the putrefied product of a lipoidal material decomposed in admixture with a lipolytic enzyme produces significant ruminant repellency. Although the invention has been specifically described and exemplified by preferred embodiments, it will be apparent to one of ordinary skill in the art that a wide variety of lipoidal materials and lipolytic enzymes can be combined to produce a putrescent ruminant repellent composition. Various substitutions of equivalents and alterations to the methods for producing and applying the repellents disclosed herein can be made without departing from the original intent and scope of the invention as disclosed. It is therefore intended that the present invention be limited only by the definition contained in the appended claims.

TABLE I

BIOASSAY RESULTS

| | Product of Example | Product % (wt) | Binder % (wt) | Water % (wt) | Test Procedure | % Browsed | Relative Repellency*** |
|---|---|---|---|---|---|---|---|
| | I | 1.5 | 13.5 | 85 | H | 10 | 100 |
| A | II | " | " | " | H | 0 | 1000 |
| | II | " | " | " | MC | " | " |
| | I | 1.5 | 13.5 | 85 | MC | 28 | 100 |
| B | | | | | | | |
| | III | " | " | " | | 0 | 2800 |
| | I | 1.5 | 13.5 | 85 | MC | 59 | 100 |
| C | | | | | | | |
| | IV | " | " | " | | 13 | 453 |
| | I | 1.5 | 13.5 | 85 | MC | 74 | 100 |
| D | | | | | | | |
| | V | " | " | " | | 19 | 390 |
| | I | 1.5 | 13.5 | 82.5* | MC | 74 | 100 |
| E | | | | | | | |
| | VI | " | " | " | | 39 | 190 |
| | I | 1.5 | 13.5 | 85 | H | 29 | 100 |
| F | I | " | "** | " | | 30 | 97 |
| | VII | " | " | " | | 0 | 2900 |
| | II | 1.5 | 13.5 | 85 | H | 40 | 100 |
| G | | | | | | | |
| | VIII | " | " | " | | 25 | 160 |

*Plus 2.5% tetramethylthiuram disulfite, a common rabbit repellent.
**Binder is Raeco No. 780 RB, defined above.
***Relative repellency is a comparison of the treated test sample with the treated control sample within each series. The control sample is given a rating of 100. Where the test sample, for example II in test set A, is unbrowsed, an assumption of 1% browsed is made for purposes of comparison.

What is claimed is:

1. A method for repelling ruminants from material normally eaten by said ruminants comprising:
   contacting said edible material with a ruminant repelling non-phytotoxic amount of a ruminant repellent composition, an active ingredient of said repellent composition comprising a putrescent product of a mixture of an animal lipoidal material and an amount of a lipolytic enzyme in excess of the lipolytic enzyme occurring naturally in said lipoidal material.

2. The method of claim 1 wherein said animal lipoidal material comprises whole fish.

3. The method of claim 2 wherein said lipoidal material further comprises fish oil in addition to fish oil present in said fish.

4. The method of claim 3 wherein said fish oil comprises from about 5% by weight to about 20% by weight of said mixture.

5. The method of claim 4 wherein said fish comprises whole salmon and said fish oil comprises tuna oil.

6. The method of claim 2 wherein said enzyme is added in an amount equivalent to at least 0.1% by weight of lipose having a potency of 3.5 times a USP unit of pancreatic enzyme.

7. The method of claim 1 wherein said lipoidal material comprises tallow.

8. The method of claim 1 wherein said lipolytic enzyme comprises pancreatic enzyme.

9. The method of claim 1 wherein said lipolytic enzyme comprises visceral enzyme from feeding fish.

10. The method of claim 1 further comprising applying said putrescent product in admixture with water and a carrier.

11. The method of claim 1 wherein said material is contacted with the active repellent component of said ruminant repellent composition, said active repellent component being obtained by:
   contacting said putrescent product with a substantially water-immiscible, organic solvent to form a solvent phase containing said active repellent component dissolved from said putrescent product,
   separating said solvent phase from said putrescent product, and
   separating said component from said solvent phase.

12. The method of claim 11, wherein said solvent comprises a halogenated hydrocarbon.

13. A method for decreasing the phytotoxicity of a ruminant repellent produced by decomposing animal lipoidal material in the presence of a lipolytic enzyme to form a putrescent product comprising:
   extracting an active repellent component from said putrescent product by
   mixing said product with a substantially water-immiscible, organic solvent to form a solvent phase;

separating said solvent phase from said putrescent product, and separating said component from said solvent by evaporation of said solvent.

14. The method of claim 13 wherein said solvent comprises a halogenated hydrocarbon.

15. The method of claim 14, wherein said solvent comprises dichloromethane, trichloroethane, carbon tetrachloride or chloroform.

16. A method of repelling ruminants from material normally eaten by said ruminants comprising:

contacting said material with a ruminant repelling non-phytotoxic amount of a ruminant repellent composition, an active ingredient of said repellent composition comprising the putrescent product of a comminuted mixture of whole salmon and lipolytic pancreatic enzyme in excess of that present in said whole salmon.

17. The method of claim 16 wherein said mixture further comprises tuna oil.

18. The method of claim 16 wherein said material is contacted with the active repellent component of said repellent composition, said active repellent component being obtained by:

extracting said putrescent product with a solvent selected from the group consisting of dichloromethane, trichloromethane, carbon tetrachloride, and chloroform to form a solvent phase containing said active repellent component dissolved from said putrescent product, separating said solvent phase from said putrescent product, and separating said component from said solvent phase.

19. A method for repelling ruminants from material normally eaten by said ruminants comprising:

contacting the region adjacent said edible material with a ruminant repelling non-phytotoxic amount of a ruminant repellent composition, an active ingredient of said repellent composition comprising a putrescent product of a mixture of an animal lipoidal material and an amount of a lipolytic enzyme in excess of the lipolytic enzyme occurring naturally in said lipoidal material.

* * * * *